United States Patent [19]

Hegasy et al.

[11] Patent Number: 4,693,892
[45] Date of Patent: Sep. 15, 1987

[54] GELATIN CONTAINING β-CAROTENE

[75] Inventors: Ahmed Hegasy, Leverkusen; Manfred Winter, Cologne, both of Fed. Rep. of Germany

[73] Assignee: Bayer Aktiengesellschaft, Leverkusen, Fed. Rep. of Germany

[21] Appl. No.: 904,733

[22] Filed: Sep. 5, 1986

[30] Foreign Application Priority Data

Sep. 10, 1985 [DE] Fed. Rep. of Germany ....... 3532129

[51] Int. Cl.$^4$ .......................... A61K 9/48; C09B 61/00
[52] U.S. Cl. ..................................... 424/456; 424/451; 514/962; 514/972; 106/288 Q; 106/304; 8/438; 8/440

[58] Field of Search .......................... 424/37, 451, 456; 8/438, 440; 514/962, 972; 106/288 Q, 304

[56] References Cited

U.S. PATENT DOCUMENTS 3,784,684 1/1974 Bossert et al. ......................... 424/37
4,268,265 5/1981 Von Wattennyl ...................... 8/440

Primary Examiner—Shep K. Rose
Attorney, Agent, or Firm—Sprung Horn Kramer & Woods

[57] ABSTRACT

Light-fast capsules for dihydropyridines such as nifedipine and nisoldipine are formed of gelatin colored with a mixture of β-carotene and iron oxide.

8 Claims, No Drawings

GELATIN CONTAINING β-CAROTENE

The invention relates to a combination of β-carotene and iron oxides as opaque coloring agent, which is fast to light, of gelatin, and to its use in foodstuffs and medicaments, in particular in the casing of soft gelatin capsules.

The foodstuff coloring agent β-carotene (Colour Index no. 40800) is soluble in oils or fats in yellowish to orange-red color. It is the main constituent of natural carotene (CI No. 75130) and is preferably used for coloring foodstuffs such as margarine or fruit beverages. A considerable disadvantage of this coloring agent is its lack of fastness to light (compare DFG Farbstoff-Kommission, Ringbuch Farbstoffe für Lebensmittel (German Research Council Commission on colouring agents, ring-file Colouring Agents for Foodstuffs)). In respect of the instability to light, it is recommended in this citation that the coloring agent be stored and in the dark under inert gas.

When β-carotene is used to color gelatin, in particular to color water-containing soft gelatin, the problem of the lack of fastness to light arises to an increased extent. The original color shade is observed to have paled after only a short time.

This instability is further increased if the soft gelatin additionally contains titanium dioxide as opacifying agent. In addition to the marked loss of color there is also a change in color from orange to pink in the presence of titanium dioxide.

Because of these properties, it has not hitherto been possible to incorporate the coloring agent β-carotene, which is biologically well tolerated, in gelatin capsules in a satisfactory manner. Particularly in cases where the coloring of the capsule casing was intended additionally to protect sensitive active compounds in the contents of the capsule from light it has not been possible to use this coloring agent because of its own lack of fastness to light.

It has been found that when a combination of β-carotene and iron oxides are used in gelatin capsules it is possible to obtain opaque colorations of great fastness to light. Particular interest attaches to a combination of 0.02 to 0.5% by weight, in particular 0.05 to 0.3% by weight, of β-carotene (based on the weight of the gelatin composition) and 0.06 to 0.5% by weight, in particular 0.15 to 0.4% by weight, of iron oxide (based on the weight of the gelatin composition). The combined coloring agent according to the invention thus contains 1–25 parts by weight of β-carotene and 3–25 parts by weight of iron oxides.

The incorporation of iron oxide and/or certain foodstuff coloring agents, such as yellow orange S (CI No. 15985), into soft gelatin as coloring and light-protection agents has already been disclosed (compare DE-OS (German Published Specification) No. 2,209,526). However, relatively large amounts, of about 1 to 2% by weight, of iron oxides are frequently necessary to attain optimum light protection. In some countries, the amount of iron in the form of iron oxides which it is permissible to administer each day to a patient is limited by conditions made by the authorities. For example, the permissible upper limit for the administration of iron in the form of iron oxides in the USA is 5 mg per day and patient. In addition, the approval of foodstuff coloring agents by the authorities, in particular the approval of representatives of azo coloring agents, is subject to restricting conditions in some countries, since a few representatives of these coloring agents are suspected of inducing side effects such as, for example, allergies.

The advantages of the combination according to the invention are that β-carotene is very well tolerated, there being virtually no restricting conditions in individual countries, and that the invention makes it possible to reduce significantly the content of iron oxides, it being ensured at the same time that there is great fastness to light and an optimum light-protection effect. Gelatin capsules which contain the combination according to the invention can be taken several times a day without the patient consuming amounts of iron which are no longer tolerable. At the same time, they can be stored over long periods without there being a change in their original color or a deterioration in their light-protection effect.

It is possible, by appropriate variation of the amount of the β-carotene which is used according to the invention, and of the amount and type of the iron oxides which are used, to prepare opaque, light-stable gelatin capsules which have an outstanding light-protection effect for the contents of the capsule and are in various color shades, for example yellow, orange, red or brown capsules.

Optionally Titaniumdioxide can be added to the shell, preferably at an amount of 0,2–2,0% (0,6–1,8%) of weight of the gelatine-glycerine shell.

To demonstrate the fastness to light, the capsules according to Example 2 of the invention are irradiated with xenon light for 24 hours. After this period, they show no sigificant change in color or paling of the original color shade.

To demonstrate the light-protecting effect, the capsules according to the invention were filled with a solution of the very light-sensitive dihydropyridine derivative nifedipine, according to Example 2, and likewise irradiated in the xenon test. After an irradiation time of 24 hours, there was no significant decomposition of the nifedipine detectable. It is also possible in this way to protect other dihydropyridines from decomposition by the action of light, for example nisoldipine.

In the text which follows, the preparation of a few gelatin capsules which contain the coloring agent combination according to the invention is described by way of example:

EXAMPLE 1 (Comparison Example without iron oxide)

Coloring with finely β-carotene 0.100 kg of β-carotene extra pure are suspended in a mixture of 0.275 kg of glycerol and 0.100 kg of water and 0.025 kg of gelatin. The suspension is added to 500 ml of glass beads in a bead mill, and the β-carotene is milled extremely finely. A red uniform suspension is produced.

The suspension is removed from the glass beads. This coloring mixture is added to 42 kg of gelatin, 28 kg of glycerol and 30 kg of water. From this are prepared soft gelatin capsules with a reddish orange color in the format 6 minims oblong (one minim corresponds to a volume of 0,06 ml) with a casing weight of about 210 mg. The filling introduced into the capsule is 377 mg of a solution of 3 parts by weight of nifedipine, 94 parts by weight of polyethylene glycol 400, 8 parts by weight of water and 8 parts by weight of glycerol per capsule.

EXAMPLE 2

Coloring with finely milled β-carotene and iron oxide

A finely milled suspension of β-carotene is prepared in analogy to Example 1. 0.5 kg of yellow iron oxide, 42 kg of gelatin, 28 kg of glycerol and 30 kg of water are added to the suspension. The gelatin composition is opaque and has an orange color. The composition is processed to form capsules with the same contents as in Example 1.

EXAMPLE 3

Coloring with water-soluble β-carotene formulations and iron oxide 28 kg of glycerol, 5 kg of water and 5 kg of gelatin are heated to 60° C. in a container. 1 kg of commercially available so-called water-soluble β-carotene (containing 10% β-carotene and 90% additives) and 0.1 kg of yellow iron oxide are incorporated. Then, a further 25 kg of water and 37 kg of gelatin are added. Capsules are prepared from this in analogy to Example 1.

EXAMPLE 4

Capsules containing 5 mg of nisoldipine per capsule are prepared in analogy to Example 3, by encapsulating 226 mg of a mixture of 2.5 parts by weight of nisoldipine with 95 parts by weight of polyethylene glycol 400 and 6 parts by weight of water and 10 parts by weight of glycerol. The capsule format is 4 minims.

EXAMPLE 5

Coloring with a solution of β-carotene in organic solvents and with iron oxide 0.1 kg of β-carotene is dissolved in 5 kg of trichloroethylene. The solution is added to a mixture of 0.2 kg of yellow iron oxide, 28 kg of glycerol, 5 kg of water and 5 kg of gelatin which has been heated to 60° C.

This β-carotene solution is homogenized, for example using a high-speed stirrer. A uniform homogeneous colored suspension is produced. This is maintained at about 60° C., and the trichloroethylene is removed. Then 37 kg of gelatin and 25 kg of water are added, and the composition is processed to form soft gelatin casings in analogy to Example 1.

EXAMPLE 6

Capsules containing 5 mg of nisoldipine 101.6 kg of polyethlene glycol 400 is heated to about 60° C. in a vessel, protecting from light. 1.334 kg of nisoldipine are dissolved in this. Then 5 kg of water, 5 kg of glycerol and 0.066 kg of pepperimint oil are added. The solution is cooled and filtered. This active compound solution is encapsulated on soft gelatin capsules each containing 424 mg of solution, corresponding to 5 mg of active compound. The capsule casing is prepared from 42.85 kg of gelatin, 26.70 kg of glycerol (Eur. Pharmacopoeia), 0.93 kg of titanium dioxide, 0.93 kg of a 10% strength β-carotene dispersion, 0.07 kg of red iron oxide and 28.50 kg of water.

EXAMPLE 7

Capsules containing 2.5 mg of nisoldipine

An active compound solution is prepared in analogy to Example 6. The solution is encapsulated with 212 mg of solution in each capsule (format 3 minims). The capsule casing consists of 42.6 kg of gelatin, 26.6 kg of glycerol, 0.93 kg titanium dioxide, 1.86 kg of a 10% strength β-carotene dispersion, 0.14 kg of yellow iron oxide and 27.0 kg of water.

EXAMPLE 8

Capsules containing 10 mg of nifedipine

A composition for the capsule casing is prepared from 40.1 kg of gelatin; 28.9 kg of glycerol; 28.9 kg of water; 1.6 kg of a 10% strength β-carotene dispersion; 1.07 kg of titanium dioxide and 0.06 kg of yellow iron oxide. An active compound solution consisting of 2.94 kg of nifedipine; 94.21 kg of polyethylene glycol 400; 6 kg of anhydrous glycerol; 10 kg of water; 0.15 kg of saccharin sodium and 0.2 kg of peppermint oil is prepared, protecting from light. 386 mg portions of the active compound solution are encapsulated in the abovementioned composition for capsule casings.

EXAMPLE 9

A two-color capsule containing 20 mg of nifedipine

Two different gelatin compositions are prepared. Composition A is identical to the composition of Example 8. Composition B consists of 42.2 kg of gelatin, 28.7 kg of glycerol; 28.7 kg of water; 0.60 kg of red iron oxide and 0.17 kg of titanium dioxide.

An active compound solution is prepared from 4.6 kg of nifedipine; 96.84 kg of polyethylene glycol 400, 6.2 kg of anhydrous glycerol; 6.0 kg of water and 1.6 kg of peppermint oil. 495 mg portions of the solution are encapsulated in capsules of size 8 minims. This entails use of one half of the casing of composition A and the other half of composition B.

It will be understood that the specification and examples are illustrative but not limitative of the present invention and that other embodiments within the spirit and scope of the invention will suggest themselves to those skilled in the art.

We claim:

1. A light-fast opaque coloring composition comprising by weight a mixture of about 1 to 25 parts of β-carotene and about 1 to 25 parts of iron oxide.

2. A composition according to claim 1, comprising by weight about 3 to 18 parts of β-carotene and about 1 to 6 parts of iron oxide.

3. A composition according to claim 1, further comprising titanium dioxide.

4. A composition according to claim 1, further comprising gelatin, the β-carotene being present in about 0.02 to 0.5% by weight of the gelatin.

5. A gelatin capsule formed of a composition according to claim 4.

6. A capsule according to claim 5, further comprising titanium dioxide.

7. A capsule according to claim 5, containing nifedipine.

8. A capsule according to claim 5, containing nisoldipine.

* * * * *

UNITED STATES PATENT AND TRADEMARK OFFICE
CERTIFICATE OF CORRECTION

PATENT NO. : 4,693,892
DATED : Sept. 15, 1987
INVENTOR(S) : Hegasy et al.

It is certified that error appears in the above-identified patent and that said Letters Patent is hereby corrected as shown below:

| | |
|---|---|
| Title Page, under "U.S. Patent Documents" | Correct spelling of -- Von Wattenwyl -- |
| Col. 1, line 20 | Insert -- cool-- after "stored" |
| Col. 1, line 52 | Delete "s" from "oxides" |

Signed and Sealed this

Tenth Day of May, 1988

Attest:

DONALD J. QUIGG

Attesting Officer

Commissioner of Patents and Trademarks